United States Patent [19]

Hayakawa et al.

[11] Patent Number: 4,871,852
[45] Date of Patent: Oct. 3, 1989

[54] QUINOLINE-CARBOXYLIC ACID DERIVATIVES

[75] Inventors: Isao Hayakawa; Shohgo Atarashi; Shuichi Yokohama; Masazumi Imamura, all of Tokyo, Japan

[73] Assignee: Daiichi Seiyaku Co., Ltd., Tokyo, Japan

[21] Appl. No.: 129,424

[22] Filed: Nov. 27, 1987

Related U.S. Application Data

[63] Continuation of Ser. No. 808,720, Dec. 13, 1985, abandoned.

[30] Foreign Application Priority Data

Dec. 14, 1984 [JP] Japan .................. 59-264221
Feb. 26, 1985 [JP] Japan .................. 60-37008

[51] Int. Cl.$^4$ ............................ C07D 401/70
[52] U.S. Cl. ........................ 544/363; 546/156
[58] Field of Search .............. 544/363; 546/156; 514/254, 312

[56] References Cited

U.S. PATENT DOCUMENTS 4,528,287 7/1985 Itoh ................................. 514/254
4,556,658 12/1985 Grohe .............................. 544/363
4,705,788 11/1987 Schriewer et al. ................ 514/254

OTHER PUBLICATIONS

Kyorin Derwent Abstract, C84-089748, (7/84).

Primary Examiner—Esther M. Kepplinger
Assistant Examiner—Robert Benson
Attorney, Agent, or Firm—Sughrue, Mion, Zinn, Macpeak & Seas

[57] ABSTRACT

Novel 4-oxoquinoline-3-carboxylic acid derivatives having the formula

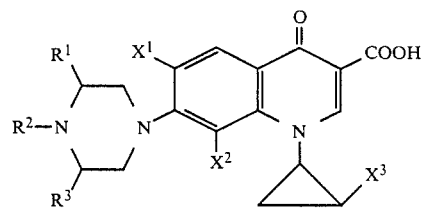

wherein $X^1$ represents a halogen or hydrogen atom, $X^2$ represents a halogen or hydrogen atom, $X^3$ represents a halogen atom, and $R^1$, $R^2$ and $R^3$ each represents a hydrogen atom or an alkyl group having 1 to 6 carbon atoms, and physiologically acceptable salts thereof, are disclosed. These compounds have excellent antibacterial activity against gram-positive and gram-negative bacteria and beneficial pharmacokinetic properties.

3 Claims, No Drawings

QUINOLINE-CARBOXYLIC ACID DERIVATIVES

This is a continuation of application Ser. No. 808,720, filed 12/13/85, now abandoned.

FIELD OF THE INVENTION

This invention relates to novel quinoline-carboxylic acid derivatives having excellent antibacterial activity.

BACKGROUND OF THE INVENTION

Hitherto, certain types of 4-oxoquinoline-3-carboxylic acid compounds having antibacterial activity have been known. For example, JP-A-58074664 (EP-A-78362) describes 1-cyclopropyl-6-fluoro-1,4-dihydro-7-(1-piperazinyl)-4-oxoquinoline-3-carboxylic acid of the formula

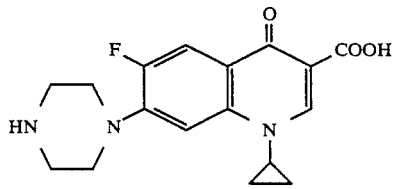

(particularly in Example 3, which is called cyprofloxacin or "Ba-2" hereinafter), and similar compounds are also disclosed in JP-A-59163369 (EP-A-117473), JP-A-59130880 (EP-A-113093) and JP-A-59212474 (EP-A-126355). Of these compounds, cyprofloxacin has been reported to have excellent properties and promisingly it will be available as commercial product in near future.

SUMMARY OF THE INVENTION

This invention relates to antibacterial quinoline-carboxylic acid derivatives having the following formula (I)

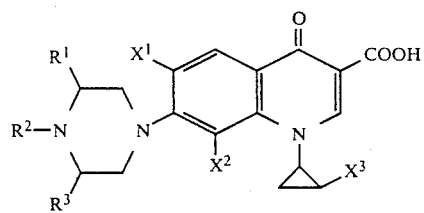

wherein $X^1$ represents a halogen or hydrogen atom, $X^2$ represents a halogen or hydrogen atom, $X^3$ represents a halogen atom, and $R^1$, $R^2$ and $R^3$ each represents a hydrogen atom or an alkyl group having 1 to 6 carbon atoms, and physiologically acceptable salts thereof.

Further, this invention relates to novel quinoline compounds having the formula (II)

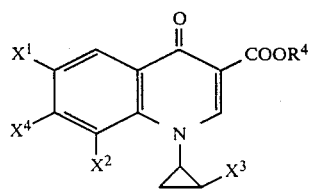

wherein $X^1$, $X^2$ and $X^3$ are as defined above, $X^4$ represents a halogen atom, and $R^4$ represents a hydrogen atom or an alkyl group having 1 to 6 carbon atoms, which are useful as intermediates to produce the compounds of formula (I) or other useful compounds.

The compound of the formula (I) has excellent antibacterial activity against gram-positive and gram-negative bacteria and has appropriate solubility in water and lipophilicity.

The term "halogen atom" as used herein for $X^1$, $X^2$ and $X^3$ means fluorine, chlorine, bromine and iodine, and fluorine is particularly preferred.

$R^1$, $R^2$ and $R^3$ each represents a hydrogen atom or an alkyl group having 1 to 6 carbon atoms, and examples of the alkyl group include methyl, ethyl, propyl and the like, with methyl being most preferred.

DETAILED DESCRIPTION OF THE INVENTION

Generally, antibacterial agents must have strong antibacterial activity and low toxicity. Further, it is necessary for the antibacterial drug to have adequate absorbability from the intestine and to provide effective blood level. In this connection, water solubility and lipophilicity of the drug are important factors, but so high lipophilicity of the drug tends to cause undesirable side effects such as insomnia, dizziness and the like. Therefore, it is much more important for such drugs to have well-balanced water solubility and lipophilicity which can be roughly estimated by determination of an apparent partition coefficient between chloroform and phosphate buffer (pH 7.4).

The rate of intestinal absorption can be determined in rat by various methods.

As a result of extensive studies, the present inventors found that the 4-oxoquinoline-3-carboxylic acid derivatives of the present invention having the formula (I) satisfy the above requirements.

The most excellent compound of this invention is 1-(cis-2-fluorocyclopropyl)-6-fluoro-1,4-dihydro-7-(4-methyl-1-piperazinyl)-4-oxoquinoline-3-carboxylic acid of the formula (Ia-1)

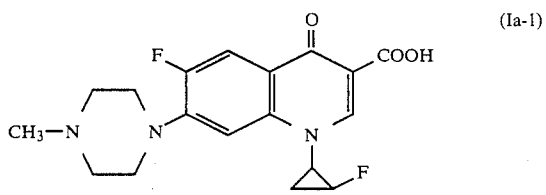

or an acid addition salt thereof, which has strong antibacterial activity and beneficial pharmacokinetic properties, i.e., high blood level and good intestinal absorption and the like, in comparison with cyprofloxacin.

The antibacterial activity (in vitro) of the compounds of this invention is shown in Table 1 in comparison with known compounds having similar structural formula such as cyprofloxacin.

The configuration between quinoline nucleus and halogen atom on the cyclopropyl group of the compound of this invention can vary to cis to trans, but cis type compound exhibits an antibacterial activity stronger than trans type compound.

The compound of this invention of the formula (I) can form an acid addition salt with an inorganic or organic acid such as hydrochloric acid, sulfuric acid, methanesulfonic acid, acetic acid, gluconic acid and the like, and also can form the corresponding carboxylate with an alkali metal or an alkaline earth metal such as sodium, potassium, calcium and the like. Further, the compound can exist as a hydrate thereof.

The compounds of this invention can be prepared by the reaction illustrated below, in which a compound having fluorines as $X^1$ and $X^3$ and hydrogen as $X^2$ is used as an example.

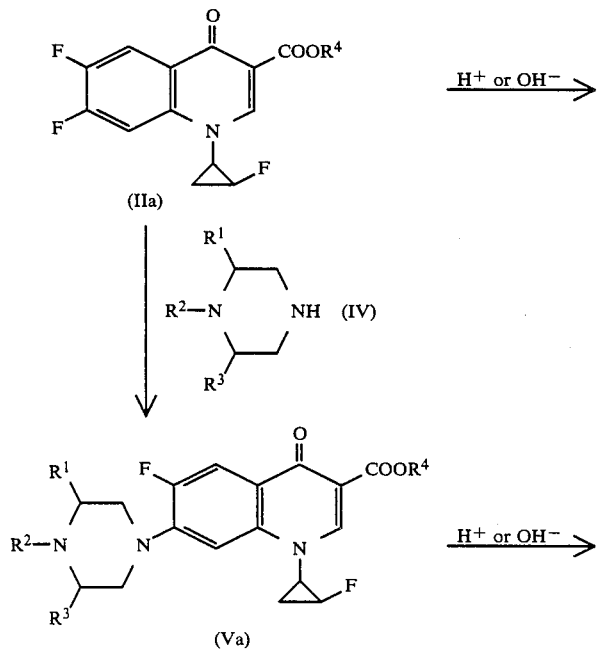

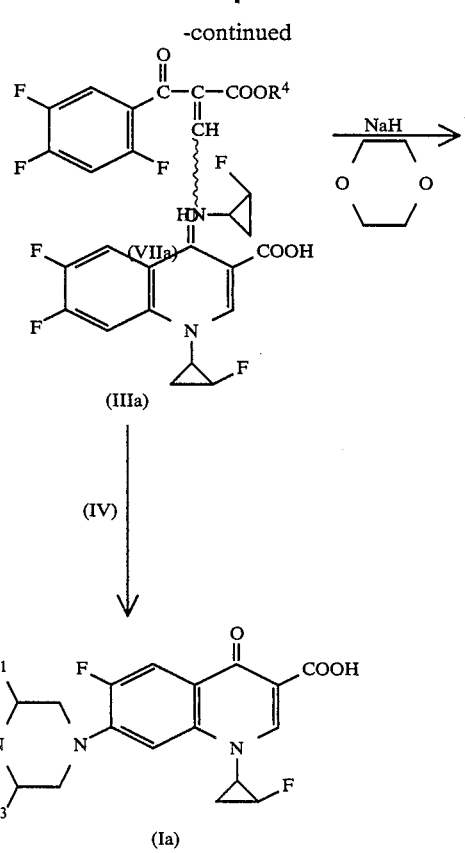

When an ester of 1-(2-fluorocyclopropyl)-6,7-difluoro-1,4-dihydro-4-oxoquinoline-3-carboxylic acid (IIa) is hydrolyzed under acidic or alkaline condition, the corresponding carboxylic acid (IIIa) can be produced, and this compound can be reacted with piperazine or a substituted piperazine (IV) to obtain the desired compound (Ia) in good yield.

These reactions can be carried out in a suitable solvent such as dimethyl sulfoxide, dimethylformamide, pyridine, 3-methoxybutanol and the like at a temperature of from room temperature to 150° C., preferably from about 40° C. to about 120° C. Each of the above reactions can be accomplished in a period from about 30 minutes to about 5 hours, normally from 30 minutes to 2 hours.

Alternatively, the compound of formula (IIa) can be reacted with piperazine or a substituted piperazine (IV), and the resulting compound of the formula (Va) can be hydrolyzed without isolation under similar conditions as described above to yield the desired compound (Ia).

As for the method for producing the starting materials, an example for the preparation of the compound (IIa) is described below:

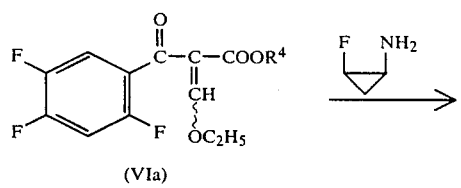

That is, ethyl 3-ethoxy-2-(2,4,5-trifluorobenzoyl)acrylate (VIa; $R^4=C_2H_5$) is reacted with 1-amino-2-fluorocyclopropane (or an acid addition salt thereof such as trifluoroacetate in the presence of at least a molar equivalent of a proper base such as triethylamine), and the resulting ethyl 3-(cis-2-fluorocyclopropyl)amino-2-(2,4,5-trifluorobenzoyl)acrylate (VIIa; $R^4=C_2H_5$) can be reacted with approximately a molar equivalent of sodium hydride in a solvent such as anhydrous dioxane at a temperature of from 20° C. to 50° C. to yield ethyl 1-(2-fluorocyclopropyl)-6,7-difluoro-1,4-dihydro-4-oxoquinoline-3-carboxylate (IIa; $R^4=C_2H_5$) in good yield.

Other starting materials of the formula (II) having substituents $X^1$, $X^2$, $X^3$, $X^4$ and $R^4$ different from those of the formula (IIa) can be prepared in a similar process to that described above.

The compound having the formula (IIa) shown above as a typical example of the starting material is a quite important raw material, since it can be converted to some novel compounds having various substituents on 7-position which are expected to have good pharmacokinetic properties as well as strong antibacterial activity.

The present invention is illustrated by the following Examples, but the invention is not limited thereto.

EXAMPLE 1

1-(cis-2-fluorocyclopropyl)-6-fluoro-1,4-dihydro-7-(4-methyl-1-piperazinyl)-4-oxoquinoline-3-carboxylic acid (1-1) To 5 ml of dimethyl sulfoxide were added 96 mg of 1-(cis-2-fluorocyclopropyl)-6,7-difluoro-1,4-dihydro-4-oxoquinoline-3-carboxylic acid and 0.5 ml of N-methylpiperazine. The mixture was stirred at 110° C. for 30 minutes and the solvent was removed by distillation in vacuo. The residue was washed several times with diethyl ether and crystallized from concentrated ammonia water-ethanol to yield 52 mg of the product. m.p. 245°–252° C. (dec.)

Analysis for $C_{18}H_{19}F_2N_3O_3 \cdot \frac{1}{2}H_2O$ Calc'd: C, 58.06; H, 5.41; N, 11.28, Found: C, 58.25; H, 5.06; N, 11.56.

NMR (DMSO-$d_6$) δ (ppm): 1.7–2.1 (2H, m, —CH$_2$—CHF), 2.38 (3H, s, $$\diagdown \!\!\!\! N\text{—}CH_3)$$

2.7 (4H, br, s, ½ proton of piperazine ring), 3.8–4.1 (1H, m,

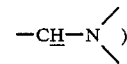

5.43 (1H, dm, J=66 Hz, —CHF), 7.55 (1H, d, J=8 Hz, C$_8$—H), 7.98 (1H, d, J=12 Hz, C$_5$—H), 8.82 (1H, s, C$_2$—H).

(1-2) In 5 ml of dimethyl sulfoxide was dissolved 62 mg of ethyl 1-(cis-2-fluorocyclopropyl)-6,7-difluoro-1,4-dihydro-4-oxoquinoline-3-carboxylate, and the mixture was heated under reflux at 110° C. for 1 hour. The solvent was removed, and the residue was washed with small quantity of water and ethanol. To the residue was added 3 ml of a mixture of acetic acid and concentrated hydrochloric acid (1:2 by volume). The mixture was heated at 120° C. for 1 hour to hydrolyze, and the solvent was removed by distillation. To the residue was added water, and the resulting precipitate was collected by filtration. After washing with ethanol and diethyl ether, the precipitate was recrystallized from concentrated ammonia water-ethanol to yield 22 mg of the product.

EXAMPLE 2

1-(cis-2-fluorocyclopropyl)-6-fluoro-1,4-dihydro-7-(1-piperazinyl)-4-oxoquinoline-3-carboxylic acid In a similar manner as described in (1-1) of Example 1, 42 mg of the product was obtained from 78 mg of the starting material. m.p. 260°–263° C. (dec.)

Analysis for $C_{17}H_{17}F_2N_3O_3 \cdot 5/4H_2O$: Calc'd: C, 54.91; H, 5.29; N, 11.30, Found: C, 54.83; H, 4.78; N, 11.22.

NMR (DMSO-$d_6$) δ (ppm): 1.7–2.2 (2H, m, —CH$_2$—CHF), 2.9–3.1 (4H, m, ½ proton of piperazine ring), 3.2–3.5 (4H, m, ½ proton of piperazine ring), 3.8–4.0 (1H, m,

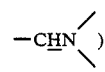

5.36 (1H, dm, J=65 Hz, —CHF), 7.48 (1H, d, J=7.5 Hz, C$_8$—H), 7.92 (1H, d, J=14 Hz, C$_5$—H), 8.76 (1H, s, C$_2$—H).

EXAMPLE 3

1-(cis-2-fluorocyclopropyl)-6-fluoro-1,4-dihydro-7-(3-methyl-1-piperazinyl)-4-oxoquinoline-3-carboxylic acid
(I; $R^1=R^2=H$, $R^3=CH_3$, $X^1=X^3=F$, $X^2=H$)

In a similar manner as described in (1-1) of Example 1, 38 mg of the product was obtained from 25 mg of the starting material. The product decomposed gradually from 240° C.

NMR (DMSO-$d_6$) δ (ppm): 1.11 (3H, d, J=7 Hz, —CH$_3$), 1.6–2.1 (2H, m, —CH$_2$—CHF), 2.9–3.7 (7H, m, proton of piperazine ring), 3.85–4.0 (1H, m,

5.37 (1H, dm, J=67 Hz, $$\diagdown \!\!\!\! CHF)$$

7.48 (1H, d, J=7 Hz, C$_8$—H), 7.94 (1H, d, J=14 Hz, C$_5$—H), 8.78 (1H, s, C$_2$—H).

EXAMPLE 4

1-(2-fluorocyclopropyl)-6,8-difluoro-1,4-dihydro-7-(4-methyl-1-piperazinyl)-4-oxoquinoline-3-carboxylic acid
(I; $R^1=R^3=H$, $R^2=CH_3$, $X^1=X^2=X^3=F$)

In 3 ml of dimethyl sulfoxide was dissolved 60 mg of 1-(2-fluorocyclopropyl)-6,7,8-trifluoro-1,4-dihydro-4-oxoquinoline-3-carboxylic acid. After addition of 100 mg of N-methylpiperazine, the mixture was stirred at 110° C. for 1 hour. The solvent was removed, and the residue was distributed between chloroform and water. The chloroform layer was dried, and the solvent was removed by distillation. The residue was crystallized from chloroform-ethanol to yield 25 mg of the product. m.p. 251°–253° C. (dec.)

Analysis for $C_{18}H_{18}F_3O_3 \cdot \frac{1}{4}H_4O$: Calc'd: C, 56.03; H, 4.83; N, 10.89, Found: C, 56.22; H, 4.70; N, 10.85.

NMR (DMSO-$d_6$) δ (ppm): 1.6–2.1 (2H, m, CH$_2$CHF), 2.28 (3H, s, —NCH$_3$), 2.51 (4H, m, ½ proton of piperazine ring), 4.1–4.3 (1H, m,

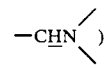

5.17 (1H, dm, J=66 Hz,

7.88 (1H, dd, J=12 Hz, 2 Hz, C$_5$—H), 8.78 (1H, s, C$_2$—H).

EXAMPLE 5

1-(2-fluorocyclopropyl)-6,8-difluoro-1,4-dihydro-7-(1-piperazinyl)-4-oxoquinoline-3-carboxylic acid (I; R$^1$=R$^2$=R$^3$=H, X$^1$=X$^2$=X$^3$=F)

In a similar manner as described in (1-1) of Example 1, 20 mg of the product was obtained from 63 mg of the starting material. m.p. 239°–245° C. (dec.)

Analysis for C$_{17}$H$_{16}$F$_3$O$_3$.¾H$_2$O: Calc'd: C, 53.61; H, 4.63; N, 11.03, Found: C, 53.38; H, 4.71; N, 10.87.

NMR (NaOD) δ (ppm): 1.6–1.9 (2H, m, —CH$_2$—CHF), 2.96, 3.35 (each 4H, m, proton of piperazine ring), 5.1–5.3 (0.5H, m, ½

7.78 (1H, dd, J=12 Hz, 2 Hz, C$_5$—H), 8.51 (1H, s, C$_2$—H).

EXAMPLE 6

1-(2-fluorocyclopropyl)-6,8-difluoro-1,4-dihydro-7-(3-methyl-1-piperazinyl)-4-oxoquinoline-3-carboxylic acid (R$^1$=R$^2$=H, R$^3$=CH$_3$, X$^1$=X$^2$=X$^3$=F)

In a similar manner as described in (1-1) of Example 1, 28 mg of colorless crystals (recrystallized from water) of the product was obtained from 35 mg of the starting material. The product decomposed gradually from 240° C.

NMR (DMSO-d$_6$) δ (ppm): 1.1 (3H, broad d, —CH$_3$), 1.6–2.1 (2H, m, —CH$_2$—CHF), 4.0–4.3 (1H, m,

5.16 (1H, dm, J=64 Hz,

7.90 (1H, dd, J=12 Hz, 2 Hz, C$_5$—H), 8.79 (1H, br, s, C$_2$—H).

EXAMPLE 7

Production of Starting Material

A suspension of 11 g of 1-bromo-2,4,5-trifluorobenzene and 6 g of cuprous cyanide in N-methylpyrrolidone was reacted in a sealed tube by heating at a bath temperature of 170° C. to 190° C. for 4 hours. The reaction mixture turned to a dark brown solution. After cooling, 500 ml of benzene was added to the solution, and the resulting precipitate was removed by filtration. The filtrate was distributed between 500 ml of benzene and water (300 ml, 300 ml and 400 ml) to remove N-methylpyrrolidone. The benzene layer was dried, and benzene was removed by distillation in vacuo. The oily residue was subjected to silica gel column chromatography, and 5.8 g of a supernatant liquid of 2,4,5-trifluorobenzonitrile was yielded from benzene eluate.

IR $\nu_{max}^{CHCl_3}$ cm$^{-1}$: 2250 (CN).

NMR $\delta_{ppm}^{CDCl_3}$: 7.05–7.35 (1H, m, C$_3$—H), 7.40–7.66 (1H, m, C$_6$—H).

In 20 ml of 80% sulfuric acid was dissolved 5.8 g of 2,4,5-trifluorobenzonitrile and the mixture was heated under reflux for 30 minutes. After cooling, the reaction mixture was poured into ice-water and extracted with ethyl acetate. The extract was dried over sodium sulfate and the solvent was removed to yield 5.32 g of 2,4,5-trifluorobenzamide.

IR $\nu_{max}^{CHCl_3}$ cm$^{-1}$: 3540, 3410 (NH$_2$), 1675 (C=O), m.p. 113°–115° C.

Without purification, the resulting crude 2,4,5-trifluorobenzamide was dissolved in 8.1 ml of concentrated sulfuric acid. To the solution 18 ml of an aqueous solution of 3.8 g of sodium nitrite was gradually added dropwise. After completion of the addition, the mixture was heated on a water bath for 30 minutes. After cooling, the mixture was extracted with chloroform, and the extract was dried over sodium sulfate. The solvent was removed by distillation to yield 5.16 g of 2,4,5-trifluorobenzoic acid. m.p. 95.5° to 96.5° C.

IR $\nu_{max}^{CHCl_3}$ cm$^{-1}$: 3450–2500 (OH), 1705 (C=O)

NMR $\delta_{ppm}^{CDCl_3}$: 6.90–7.25 (1H, m, C$_3$—H), 7.71–8.00 (1H, m, C$_6$—H), 11.05 (1H, s, COOH).

To 20 ml of anhydrous benzene were added 3.4 g of 2,4,5-trifluorobenzoic acid and 10 ml of thionyl chloride, and the mixture was refluxed for 2 hours. After removing the solvent, excess thionyl chloride was removed three times as an azeotropic mixture with benzene to obtain 2,4,5-trifluorobenzoyl chloride.

On the other hand, a suspension of magnesium ethoxide and 3.1 g of diethyl malonate in 30 ml of anhydrous diethyl ether was refluxed for 1 hour. To the cooled suspension was added dropwise 15 ml of an anhydrous diethyl ether solution of 2,4,5-trifluorobenzoyl chloride obtained above with stirring. The resulting mixture was stirred at room temperature for 1 hour. After acidification with diluted hydrochloric acid, the mixture was extracted with 150 ml of ethyl acetate (50 ml×3). The extract was dried over sodium sulfate, and the solvent was removed by distillation. The resulting residue was dissolved in 50 ml of dioxane and a catalytic amount of p-toluenesulfonic acid was added thereto. The mixture was refluxed for 24 hours and, after cooling, the reaction mixture was neutralized with an aqueous sodium bicarbonate solution and extracted with 200 ml of chloroform. The extract was dried over sodium sulfate, and the solvent was removed. The residue was subjected to silica gel column chromatography and 2.1 g of ethyl 2,4,5-trifluorobenzoylacetate was yielded from benzene eluate.

IR $\nu_{max}^{CHCl_3}$ cm$^{-1}$: 1735 and 1690 (C=O)

NMR $\delta_{ppm}^{CDCl_3}$: 1.27 (½×3H, t, J=6.5 Hz, ½×CHCH$_3$), 1.36 (½×3H, t, J=6.5 Hz, ½×CH$_2$CH$_3$), 3.95 (½×2H, d, J=3.2 Hz, COCH$_2$CO$_2$Et), 4.22 (½×2H, q, J=6.5 Hz, ½×—CH$_2$CH$_3$), 4.28 (½×2H, q, J=6.5 Hz, ½×—CH$_2$CH$_3$), 5.82 (½×1H, s,

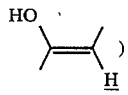

6.83–7.20 (1H, m, $C_3$—H), 7.55–7.90 (1H, m, $C_6$—H), 12.69 (½H, s, —OH).

A solution of 1.36 g of ethyl 2,4,5-trifluorobenzoylacetate and 5.1 ml of an acetic anhydride solution of 1 ml ethyl orthoformate were heated under reflux for 1 hour. The solvent was removed by distillation, and the residue was thoroughly dried in vacuo to yield a cis-trans mixture of ethyl 3-ethoxy-2-(2,4,5-trifluorobenzoyl)acrylate.

NMR (CDCl$_3$) δ (ppm): 1.0–1.58 (6H, m, —CH$_2$CH$_3$×2), 3.98–4.58 (4H, m, —CH$_2$CH$_3$×2), 6.70–7.48 (2H, m, aromatic proton), 7.76 & 7.90 (each 0.5H, s, cis and trans of

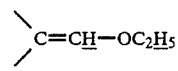

In 7 ml of methylene chloride were dissolved 650 mg of the cis-trans mixture obtained above and 620 mg of cis-1-amino-2-fluorocyclopropane.trifluoroacetate.
After addition of 2.4 ml of triethylamine, the resulting mixture was stirred at room temperature for 1 hour. The solvent was removed, and the residue was subjected to column chromatography using 30 g of silica gel. From chloroform eluate, 540 mg of ethyl trans-2-fluorocyclopropylamino-2-(2,4,5-trifluorobenzoyl)acrylate (VIIa; R$^4$=C$_2$H$_5$) was yield. m.p. 91°–92° C.

Analysis for C$_{15}$H$_{13}$F$_4$NO$_3$: Calc'd: C, 54.39; H, 3.96; N, 4.23, Found: C, 54.40; H, 3.96; N, 4.27.

NMR (CDCl$_3$) δ (ppm): 1.09 (3H, t, J=7 Hz, —CH$_3$) 1.2–1.5 (2H, m, —CH$_2$—CHF) 2.9–3.1 (1H, m, —CH—NH—) 4.10 (2H, q, J=7 Hz, —CH$_2$CH$_3$) 4.75 (1H, dm, J=64 Hz, —CHF) 6.8–7.0 (1H, m, aromatic proton) 7.2–7.4 (1H, m, aromatic proton) 8.27 (1H, d, J=14 Hz, olefinic proton) 10.8–11.0 (1H, m, —NH)

In 10 ml of anhydrous dioxane were dissolved 260 mg of the product obtained above and 38 mg of 50% sodium hydride under stirring at room temperature. After 30 minutes, dioxane was removed by distillation and chloroform was added thereto. The mixture was washed with 10% citric acid and 1N hydrochloric acid and water, and then dried over sodium sulfate. The solvent was removed by distillation in vacuo to yield 245 mg of a slightly yellow solid of ethyl 1-(cis-2-fluorocyclopropyl)-6,7-difluoro-1,4-dihydro-4-oxoquinoline-3-carboxylate (IIa; R$^4$=C$_2$H$_5$).

NMR (CDCl$_3$) δ (ppm): 1.40 (3H, t, J=7 Hz, —CH$_3$), 1.5–1.9 (2H, m, —CH$_2$—CHF), 3.2–3.7 (1H, m,

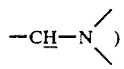

4.39 (2H, q, J=7 Hz, —CH$_2$CH$_3$), 5.14 (1H, dm, J=61 Hz, —CHF), 7.64 (1H, dd, J=11 Hz, 7 Hz, C$_8$—H), 8.24 (1H, dd, J=11 Hz, 8.5 Hz, C$_5$—H), 8.60 (1H, s, C$_2$—H).

In 12 ml of a mixture of acetic acid and concentrated hydrochloric acid (1:2 by volume) was dissolved 245 mg of the compound obtained above, and the resulting mixture was heated at 120° C. for 30 minutes. After cooling, water was added to the mixture, and the resulting precipitate was collected by filtration. After washing with ethanol and diethyl ether, the precipitate was dried to obtain 175 mg of colorless crystals of 1-(cis-2-fluorocyclopropyl)-6,7-difluoro-1,4-dihydro-4-oxoquinoline-3-carboxylic acid (IIIa; R$^4$=C$_2$H$_5$). m.p. 249°–252° C.

NMR (CDCl$_3$) δ (ppm): 1.7–1.95 (2H, m, —CH$_2$—CHF), 3.5–3.7 (1H, m,

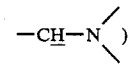

5.19 (1H, dm, J=64 Hz, —CHF), 7.82 (1H, dd, J=12 Hz, C$_8$—H), 8.37 (1H, dd, J=11 Hz, 8.5 Hz, C$_5$—H), 8.94 (1H, s, C$_2$—H), 14.45 (1H, br, s, —COOH).

EXAMPLE 8

Production of Starting Material

In 5 ml of methylene chloride were dissolved 850 mg of ethyl 3-ethoxy-2-(2,3,4,5-tetrafluorobenzoyl)acrylate and 700 mg of 1-amino-2-fluorocyclopropane trifluoroacetate. After addition of 1 ml of triethylamine, the mixture was stirred at room temperature for 1 hour. The solvent was removed by distillation, and the residue was purified by column chromatography using 40 g of silica gel. From the chloroform eluate 450 mg of ethyl 3-(2-fluorocyclopropyl)amino-2-(2,3,4,5-tetrafluorobenzyl)acrylate was obtained.

NMR (CDCl$_3$) δ (ppm): 0.8–1.6 (5H, m, —CH$_3$, —CH$_2$—CHF), 2.9–3.2 (1H, m, —CH—NH—), 4.07 (2H, q, J=7 Hz, —CH$_2$CH$_3$), 4.72 (2H, dm, J=62 Hz,

6.8–7.2 (1H, m, aromatic proton), 8.2, 8.36 (each 0.5H, s, olefinic proton).

To anhydrous dioxane, 400 mg of the product obtained above and 55 mg of 50% sodium hydride were added portionwise to dissolve under cooling with cold water. After 20 minutes, the reaction mixture was poured into ice-water and weakly acidified with acetic acid. The mixture was extracted with chloroform, and the extract was dried over sodium sulfate. The solvent was removed, and the residue was washed with diethyl ether to yield 340 mg of colorless crystals of ethyl 1-(2-fluorocyclopropyl)-6,7,8-trifluoro-1,4-dihydro-4-oxoquinoline-3-carboxylate. m.p. 200°–201° C.

NMR (CDCl$_3$) δ (ppm): 1.42 (3H, t, J=7 Hz, —CH$_3$), 1.55–1.90 (2H, m, —CH$_2$CHF), 3.6–4.0 (1H, m,

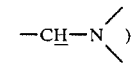

4.42 (2H, q, J=7 Hz, —CH$_2$CH$_3$), 4.95 (1H, dm, J=63 Hz, —CHF), 8.16 (1H, ddd, J=11 Hz, 8.5 Hz, 3 Hz, C$_5$—H), 8.6 (1H, s, C$_2$—H).

In 4.5 ml of a mixture of acetic acid and concentrated hydrochloric acid (2:1 by volume) was dissolved 380 mg of the compound obtained above, and the resulting mixture was heated at 120° C. for 30 minutes. After cooling, water was added thereto, and the resulting precipitate was collected by filtration. The precipitate was washed with ethanol and diethyl ether and dried to yield 163 mg of 1-(2-fluorocyclopropyl)-6,7,8-trifluoro-1,4-dihydro-4-oxoquinoline-3-carboxylic acid. m.p. 232°–235° C.

NMR (CDCl₃) δ (ppm):
1.5–2.0 (2H, m, —CH₂CHF), 3.8–4.1 (1H, m,

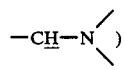

5.0 (1H, dm, J=63 Hz, —CHF), 8.17 (1H, ddd, J=10.5 Hz, 8 Hz, 3 Hz, C₅—H), 8.88 (1H, s, C₂—H).

4.6–5.1 (1H, m, —NH—).

To 800 mg of the product was added 2 ml of trifluoroacetic acid, and the mixture was stirred at room temperature for 30 minutes. Any excess trifluoroacetic acid was removed by distillation in vacuo, and 750 mg of cis-1-amino-2-fluorocyclopropane trifluoroacetate was yielded in a form of partially crystalline colorless oil.

NMR (D₂O) δ (ppm): 0.8–1.5 (2H, m, —CH₂—), 2.4–2.8 (1H, m,

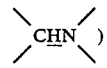

4.85 (1H, dm, J=63 Hz, CHF)

TABLE 1

| | \multicolumn{8}{c}{Minimum Inhibitory Concentration (MIC, microgram per milliliter)} |
|---|---|---|---|---|---|---|---|---|
| | \multicolumn{8}{c}{Compound} |
| | Ia-1 | Ia-2 | Ib-1 | Ib-2 | Ba-1 | Ba-2 | Ba-3 | Ba-4 |
| *Escherichia coli* NIHJ | ≦0.05 | ≦0.05 | ≦0.05 | ≦0.05 | ≦0.05 | ≦0.05 | ≦0.05 | ≦0.05 |
| *Proteus vulgaris* 3167 | ≦0.05 | ≦0.05 | ≦0.05 | ≦0.05 | ≦0.05 | ≦0.05 | ≦0.05 | ≦0.05 |
| *Serratia marcessens* 13001 | ≦0.05 | ≦0.05 | ≦0.05 | ≦0.05 | 0.10 | ≦0.05 | ≦0.05 | ≦0.05 |
| *Pseudomonas aeruginosa* 2131 | 0.20 | ≦0.05 | 0.10 | ≦0.05 | 0.10 | ≦0.05 | 0.20 | ≦0.05 |
| *Pseudomonas cepacia* IID 1340 | 0.20 | 1.56 | 0.78 | 1.56 | 0.78 | 3.13 | 0.78 | 0.39 |
| *Pseudomonas maltophilia* IID 1275 | 0.20 | 0.78 | 0.10 | 0.78 | 0.20 | 0.78 | ≦0.05 | 0.39 |
| *Staphylococcus aureus* Smith | ≦0.05 | 0.10 | 0.10 | 0.10 | 0.20 | 0.10 | 0.20 | 0.20 |
| *Staphylococcus epidermidis* 56556 | 0.10 | 0.20 | 0.20 | 0.20 | 0.39 | 0.20 | 0.20 | 0.20 |
| *Streptococcus faecalis* ATCC 19433 | 0.78 | 1.56 | 0.78 | 1.56 | 0.78 | 0.78 | 0.78 | 0.78 |

Determined by the standard method of the Japan Society of Chemotherapy: in Muller-Hinton bouillon, 10⁶/ml of bacteria were seeded and incubated at 37° C. for 18 hours.
Ia-1: 1-(cis-2-fluorocyclopropyl)-6-fluoro-1,4-dihydro-7-(4-methyl-1-piperazinyl)-4-oxoquinoline-3-carboxylic acid
Ia-2: 1-(cis-2-fluorocyclopropyl)-6-fluoro-1,4-dihydro-7-(1-piperazinyl)-4-oxoquinoline-3-carboxylic acid
Ib-1: 1-(cis-2-fluorocyclopropyl)-6,8-difluoro-1,4-dihydro-7-(4-methyl-1-piperazinyl)-4-oxoquinoline-3-carboxylic acid
Ib-2: 1-(cis-2-fluorocyclopropyl)-6,8-difluoro-1,4-dihydro-7-(1-piperazinyl)-4-oxoquinoline-3-carboxylic acid
Ba-1: 1-cyclopropyl-6-fluoro-1,4-dihydro-7-(4-methyl-1-piperazinyl)-4-oxoquinoline-3-carboxylic acid (EP-78362-A)
Ba-2: 1-cyclopropyl-6-fluoro-1,4-dihydro-7-(1-piperazinyl)-4-oxoquinoline-3-carboxylic acid hydrochloride (EP-78362-A; cyprofloxacin hydrochloride)
Ba-3: 1-cyclopropyl-6,8-difluoro-1,4-dihydro-7-(4-methyl-1-piperazinyl)-4-oxoquinoline-3-carboxylic acid (EP-126355-A)
Ba-4: 1-cyclopropyl-6,8-difluoro-1,4-dihydro-7-(1-piperazinyl)-4-oxoquinoline-3-carboxylic acid (EP-126355-A)

EXAMPLE 9

Production of Starting Material

In 30 ml of tert-butanol was dissolved 2 g of cis-2-fluoro-1-cyclopropanecarboxylic acid. After addition of 8 g of diphenylphosphorylazide (DPPA) and 3 g of triethylamine, the resulting mixture was heated under reflux for 8 hours. After removing the solvent, the residue was subjected to column chromatography using 50 g of silica gel, and 900 mg of 1-tert-butoxycarbonylamino-2-fluorocyclopropane was obtained from chloroform eluate. After allowing to stand, the crystals were washed with n-hexane to yield a sublimatic colorless crystals. m.p. 58°–60° C.

The configuration between 1- and 2-position of the product was determined as cis by X-ray analysis.

NMR (CDCl₃) δ (ppm): 0.6–1.3 (2H, m, —CH₂—), 1.45 (9H, s, —CH₃×3), 2.45–2.8 (1H, m,

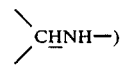

4.54 (2H, dm, J=63 Hz,

While the invention has been described in detail and with reference to specific embodiments thereof, it will be apparent to one skilled in the art that various changes and modifications can be made therein without departing from the spirit and scope thereof.

What is claimed is:

1. A compound having the formula

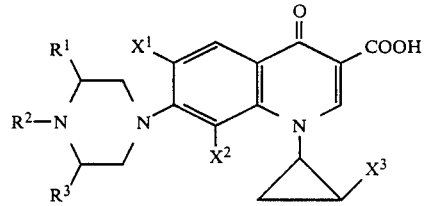

wherein X¹ represents a fluorine atom, X² represents a fluorine or hydrogen atom, X³ represents a fluorine atom, and R¹ and R³ each represents a hydrogen atom, and R² represents a methyl group or an ethyl group, the quinoline moiety and the X³ moiety being bonded to cyclopropane in the cis configuration, and physiologically acceptable salt thereof.

2. A compound as in claim 1, wherein X¹ and X³ each represents fluorine and X² represents fluorine.

3. A compound as in claim 1, which is 1-(cis-2-fluorocyclopropyl)-6-fluoro-1,4-dihydro-7-(4-methyl-1-piperazinyl)-4-oxoquinoline-3-carboxylic acid and a physiologically acceptable salt thereof.

* * * * *